(12) United States Patent
Bellezza et al.

(10) Patent No.: US 9,398,861 B2
(45) Date of Patent: Jul. 26, 2016

(54) METHODS AND DEVICES FOR ASSESSING INTRACRANIAL PRESSURE

(75) Inventors: Anthony Bellezza, Cherry Hill, NJ (US); William Lai, Philadelphia, PA (US)

(73) Assignee: Third Eye Diagnostics, Inc., Bethlehem, PA (US)

( * ) Notice: Subject to any disclaimer, the term of this patent is extended or adjusted under 35 U.S.C. 154(b) by 1045 days.

(21) Appl. No.: 12/959,821

(22) Filed: Dec. 3, 2010

(65) Prior Publication Data
US 2011/0137182 A1 Jun. 9, 2011

Related U.S. Application Data

(60) Provisional application No. 61/266,579, filed on Dec. 4, 2009.

(51) Int. Cl.
| | | |
|---|---|---|
| *A61B 5/03* | (2006.01) | |
| *A61B 5/00* | (2006.01) | |
| *A61B 8/04* | (2006.01) | |
| *A61B 8/06* | (2006.01) | |
| *A61B 8/10* | (2006.01) | |
| *A61B 6/03* | (2006.01) | |
| *A61B 6/00* | (2006.01) | |
| *A61B 8/00* | (2006.01) | |
| *A61B 8/08* | (2006.01) | |

(52) U.S. Cl.
CPC .............. *A61B 5/031* (2013.01); *A61B 5/4029* (2013.01); *A61B 8/04* (2013.01); *A61B 8/06* (2013.01); *A61B 8/10* (2013.01); *A61B 6/03* (2013.01); *A61B 6/504* (2013.01); *A61B 8/0808* (2013.01); *A61B 8/4472* (2013.01)

(58) Field of Classification Search
CPC .......... A61B 5/031; A61B 8/0808; A61B 8/06
USPC .................................... 600/485, 561
See application file for complete search history.

(56) References Cited

U.S. PATENT DOCUMENTS

| | | | | |
|---|---|---|---|---|
| 6,120,460 A | * | 9/2000 | Abreu ........................... | 600/558 |
| 6,129,682 A | * | 10/2000 | Borchert et al. .............. | 600/561 |
| 7,122,007 B2 | | 10/2006 | Querfurth | |
| 7,547,283 B2 | * | 6/2009 | Mourad et al. ................ | 600/459 |
| 8,366,627 B2 | * | 2/2013 | Kashif et al. .................. | 600/485 |
| 2002/0095087 A1 | * | 7/2002 | Mourad et al. ................ | 600/442 |
| 2004/0230124 A1 | * | 11/2004 | Querfurth ..................... | 600/485 |
| 2006/0206037 A1 | * | 9/2006 | Braxton .................... | A61B 3/12 600/561 |
| 2006/0211942 A1 | * | 9/2006 | Hoctor ............... | A61B 5/02125 600/438 |
| 2010/0280372 A1 | * | 11/2010 | Poolman et al. .............. | 600/437 |
| 2013/0144185 A1 | * | 6/2013 | Fuller .................... | A61B 5/031 600/561 |
| 2013/0211285 A1 | * | 8/2013 | Fuller ...................... | A61B 3/16 600/561 |

OTHER PUBLICATIONS

Kimberly et al. "Correlation of Optic Nerve Sheath Diameter with Direct Measurement of Intracranial Pressure." Society for Academic Emercency Medicine. vol. 15, No. 2. Feb. 2008.*

(Continued)

*Primary Examiner* — Adam J Eiseman
(74) *Attorney, Agent, or Firm* — Baker & Hostetler LLP

(57) ABSTRACT

Provided are methods for noninvasively assessing intracranial pressure ("ICP") based on optic nerve sheath diameter ("ONSD") and a blood velocity metric, such as pulsatility or resistivity index. Also provided are related devices and systems for performing the claimed methods.

15 Claims, 3 Drawing Sheets

(56) References Cited

OTHER PUBLICATIONS

Newman et al. "MEasurement of Optic Nerve Sheath Diameter by Ultrasound: a Means of Detecting Acute Rasied Intracranial Pressure in Hydrocephalus." Ophthalmol. pp. 1109-1113. 2002.*
"American Ambulance Association's Ambulance Facts", http://www.the-aaa.org/media/ambulance_facts.html, ambulance fact sheet 8-6-04.doc, accessed Sep. 15, 2007.
"American College of Emergency Physicians Web Site", http://www.acep.org/PrintFriendly.aspx?id=25214#ed, accessed Mar. 30, 2011, 11 pages.
"Association of Air Medical Services Data", http://www.aams.org/AAMS/Media_Room/Fact_Sheets FAQs/AAMS/MediaRoom/FactSheetsandFAQs/Fact_ Sheets_ and_ FAQs.aspx?hkey=4ca2897d-5805-4ae4-bd31-e9e50e7e2981, accessed Oct. 3, 2007. This site lists detailed information on its members' aircraft; it shows 530 rotor wing and 182 fixed wing aircraft at the present time. We believe this is a lower limit on the total number of these aircraft since not all operators may be members.
"Correlation of Sonographic Measurement of Optic Nerve Sheath Diameter with Invasive Intracranial Pressure Monitoring", St. Luke's Hospital, Bethlehem, PA. Protocol ID: SLHN2007-72, Sep. 10, 2008.
"The Brain Trauma Foundation. The American Association of Neurological Surgeons. The Joint Section on Neurotrauma and Critical Care. Recommendations for Intracranial Pressure Monitoring Technology", J. Neurotrauma, Jun.-Jul. 2000, 17(6-7), 497-506.
"A Non-Invasive Assessment of Intracranial Pressure in Stroke and Head Injury", IRB Approval Letter, St. Luke's Hospital, Bethlehem, PA. Protocol ID: SLHN2008-47, Nov. 25, 2008.
"Critical Care Statistics in the United States", Society of Critical Care Medicine, Jun. 2006, http://www.sccm.org/NR/rdonlyres/A5FA7249-38BB-4D0F-A518-2FB1B0B00ACC/299/WebStatisticsPamphletFinalJune06.pdf, accessed Sep. 8, 2007.
Bellezza et al., "Anterior Scleral Canal Geometry in Pressurised (IOP 10) and Non-Pressurised (IOP 0) Normal Monkey Eyes", Br. J Ophthalmol, Oct. 2003, 87(10), 1284-1290.
Bellezza et al., "Deformation of the Lamina Cribrosa and Anterior Scleral Canal Wall in Early Experimental Glaucoma", Invest Ophthalmol Vis Sci., Feb. 2003, 44(2), 623-637.
Bellezza, "Biomechanical Properties of the Normal and Early Glaucomatous Optic Nerve Head: An Experimental and Computational Study Using the Monkey Model", Ph.D. Thesis, Tulane University, Department of Biomedical Engineering, 2002.
Blaivas et al., "Elevated Intracranial Pressure Detected by Bedside Emergency Ultrasonography of the Optic Nerve Sheath", Academic Emergency Medicine, Apr. 2003, 10(4), 376-381.
Burgoyne et al., "Three Dimensional Reconstruction of the Normal and Early Glaucoma Monkey Optic Nerve Head Connective Tissues", Invest Ophthalmol Vis Sci, Dec. 2004,45(12), 4388-4399.
Burgoyne et al., "The Optic Nerve Head as a Biomechanical Structure: A New Paradigm for Understanding the Role of IOP-related Stress and Strain in the Pathophysiology of Glaucomatous Optic Nerve Head Damage", Progress in Retinal and Eye Research, Jan. 2005, 24(1), 39-73.
Czosnyka et al., "Monitoring and Interpretation of Intracranial Pressure", J. Neurol. Neurosurg. Psychiatry, Jun. 2004, 75(6), 813-821.
Defense and Veterans Brain Injury Center Website on Blast Injury, http://www.dvbic.org/blastinjury.html.
Goel et al., "Utility of Optic Nerve Ultrasonography in Head Injury", Injury, Int. J. Care Injured, May 2008, 39(5), 519-524.
Hansen et al., "Validation of the Optic Nerve Sheath Response to Changing Cerebrospinal Fluid Pressure: Ultrasound Findings During Intrathecal Infusion Tests", Journal of Neurosurgery, Jul. 1997, 87(1), 34-40.
Hayreh, "Pathogenesis of Oedema of the optic Disc (Papilloedema). A Preliminary Report", Brit. J. Ophthalmol., 1964, 48, 522-543.
Heickell et al., "Optic Disc Surface Compliance Testing Using Confocal Scanning Laser Tomography in the Normal Monkey Eye", J Glaucoma, Oct. 2001, 10(5), 369-382.
Langlois, "Traumatic Brain Injury in the United States: ER visits, Hospitalizations, and Deaths", Centers for Disease Control and Prevention, Oct. 2004, http://cdc.gov/traumaticbraininjury.
Narayan et al., "Clinical Trials in Head Injury", Journal of Neurotrauma, May 2002, 19(5), 503-557.
Querfurth et al., "Flow Velocity and Pulsatility of the Ocular Circulation in Chronic Intracranial Hypertension", Acta Neurol Scand, Jun. 2002, 105(6), 431-440.
Querfurth et al., "Prediction of Intracranial Pressure From Noninvasive Transocular Venous and Arterial Hemodynamic Measurements", Neurocritical Care, 2004, 1(2), 183-194.
The Internet Stroke Center Website http://strokecenter.org/patients/stats.htm 1997-2010.
Soldatos et al., "Optic Nerve Sonography in the Diagnostic Evaluation of Adult Brain Injury", Critical Care, May 13, 2008,12(3), 1-7.
Steiner et al., "Monitoring the Injured Brain: ICP and CBF", British Journal of Anaesthesia, Jul. 2006, 97(1), 26-38.
Tayal et al., "Emergency Department Sonographic Measurement of Optic Nerve Sheath Diameter to Detect Findings of Increased Intracranial Pressure in Adult Head Injury Patients", Ann Emerg Med., Apr. 2007, 49(4), 508-514.

* cited by examiner

METHODS AND DEVICES FOR ASSESSING INTRACRANIAL PRESSURE

RELATED APPLICATIONS

This application claims priority to U.S. Application No. 61/266,579, "Ultrasound-based Traumatic Brain Injury Screening Devices and Methods," filed on Dec. 4, 2009, the entirety of which is incorporated herein by reference for all purposes.

TECHNICAL FIELD

The present invention relates to the field of ophthalmic instrumentation and to the field of intracranial pressure measurement.

BACKGROUND

Monitoring of intracranial pressure ("ICP") for instantaneous pressure as well as for changes in pressure—especially among patients with head injury, stroke edema, or acute intracranial hemorrhage—provides important information on which to base medical and surgical treatment. Elevations in intracanial pressure may inhibit the supply of blood to the brain, causing tissue damage and possible fatality if left untreated.

The rapid detection of elevated intracranial pressure (EICP) in patients with head trauma and spontaneous intracranial hemorrhage is critical for physicians and first responders to develop the best therapy to reduce death and disability. In the field where CT scanning is unavailable, or where many patients require rapid triage (e.g., combat theater, disaster scenes, multi-casualty occurrences), a noninvasive method that could be performed quickly and does not require the experienced judgment of an image would be useful to determine whether a patient's ICP is elevated or changing.

Existing ICP monitoring devices require a neurosurgeon to drill a hole in the patient's skull for the insertion of an intracranial catheter through which one measures ICP. The types of invasive devices currently in use include intraventricular catheters, fiber optic monitors, subarachnoid bolts, and epidural monitors. Despite the risk of hemorrhage, malfunction, herniation, infection, and the expensive cost, the use of intracranial catheters remains standard method for diagnosing intracranial hypertension.

An alternative option for measurement of ICP is to puncture the lumbar dura (i.e., perform a spinal tap) to measure cerebrospinal fluid ("CSF") pressure. CSF pressure can serve as a proxy for ICP.

Because of the risks inherent in these invasive procedures, other methods have been developed to address conditions where intracranial catheters are not feasible. Some noninvasive techniques include computed tomography ("CT") scan of the head, ophthalmoscopy, and transcranial Doppler ("TCD") sonography. Each of these techniques, however, has drawbacks.

A CT scan of the head is time consuming and requires transfer of critically ill patients and supporting devices to specialized facilities. Ophthalmoscopy necessitates experienced examiners. TCD also requires well trained observers.

Accordingly, there is a need in the art for noninvasive methods of accurately assessing ICP over a range of pressures and for related devices for performing such methods.

SUMMARY

In meeting the described challenges, the present invention provides methods and devices for evaluating intracranial pressure non-invasively as it relates to brain injury by measuring optic nerve sheath diameter ("ONSD") and arterial pulsatility.

The claimed methods include locating a periocular blood vessel; locating the optic nerve; obtaining optic nerve sheath diameter and blood velocity information from a periocular blood vessel; and assessing intracranial pressure based on the optic nerve sheath diameter and blood velocity information.

The present invention also provides devices. The inventive devices suitably include a component configured to obtain optic nerve sheath diameter and blood velocity information from a periocular blood vessel, a component configured to, based on the optic nerve sheath diameter and blood velocity information, produce an assessment of the subject's intracranial pressure.

The present invention also provides systems. These systems suitably include a first device configured to obtain, from a subject, optic nerve sheath diameter information; a second device configured to obtain, from a subject, blood velocity information from a periocular blood vessel, and the system further configured to, based on the optic nerve sheath diameter and blood velocity information, produce an assessment of the subject's intracranial pressure.

BRIEF DESCRIPTION OF THE DRAWINGS

The summary, as well as the following detailed description, is further understood when read in conjunction with the appended drawings. For the purpose of illustrating the invention, there are shown in the drawings exemplary embodiments of the invention; however, the invention is not limited to the specific methods, compositions, and devices disclosed. In addition, the drawings are not necessarily drawn to scale. In the drawings.

DETAILED DESCRIPTION OF THE INVENTION

Figure 1:
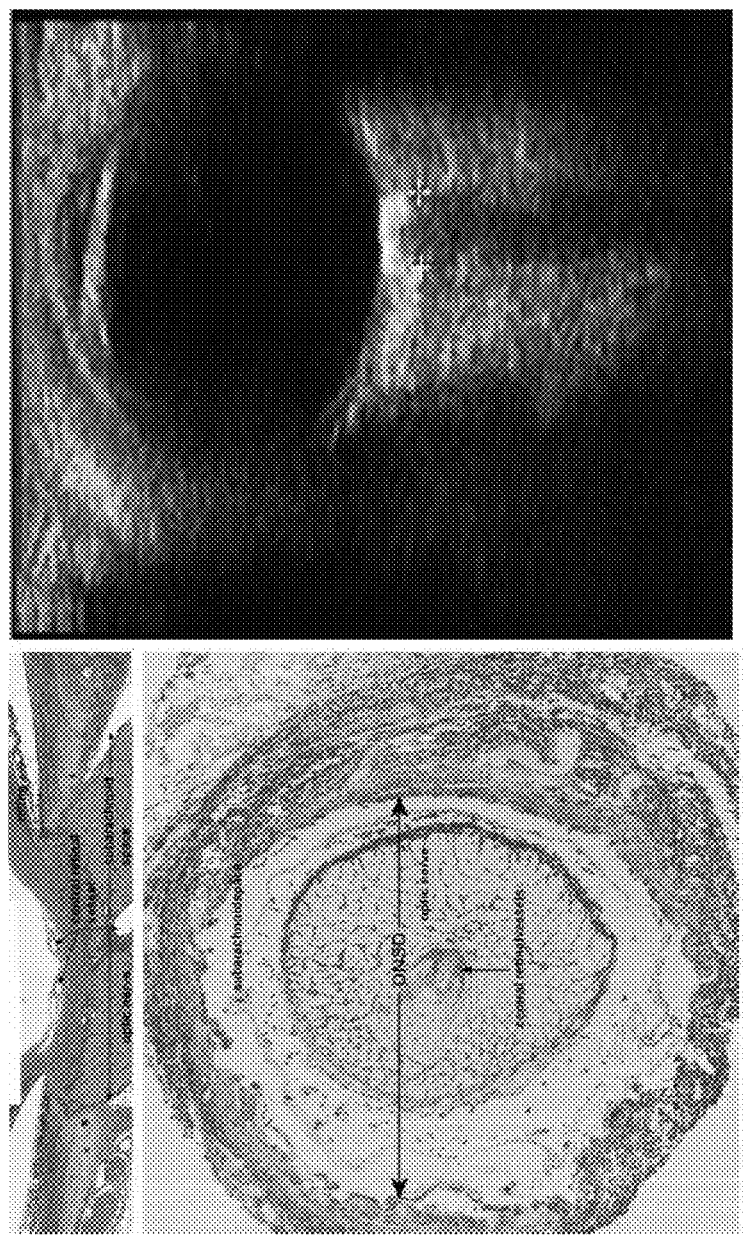
FIG. 1 illustrates images of various portions of ophthalmic anatomy.

The present invention may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further, reference to values stated in ranges includes each and every value within that range.

Additional Background—Optical Structure

The optic nerve is a bundle of individual axons that in turn connect the retinal ganglion cells to the brain. The optic nerve leaves the posterior of the eye at the scleral canal and travels to the optic chiasm. The optic nerve sheath surrounds the optic nerve, and encloses cerebrospinal fluid. An increase in cerebrospinal fluid pressure (which is equivalent to intracranial pressure) causes a distention of the optic nerve sheath ("ONS"), as shown in attached FIG. 1, which figure is adapted from Blavias et al., Acad. Emeg. Med. 2003: 10:376-381.

The subarachnoid space that surrounds the optic nerve and is within the optic nerve sheath is continuous with the subarachnoid space that surrounds the brain, which contains cerebrospinal fluid. ONS distention depends on the transfer of CSF from the intracranial space to the periocular space. As intracranial pressure increases, CSF fills the subarachnoid space within the ONS, resulting in an increased diameter.

Some have proposed using optic nerve sheath diameter ("ONSD") measurements to evaluate the head injured patient prior to transport to a CT scan, as changes in ONS can be correlated with changes in CSF pressure. Anatomically, the optic nerve sheath (ONS) is continuous with the dura, arachnoid, and pia mater, which makes it possible to correlate changes in the ONS with changes in the cerebrospinal fluid (CSF) pressure. As CSF pressure increases, Hansen et al. (J. Neurosurg. 1997; 87:34-40) demonstrated that the diameter of the ONS increases. ONSD diameters greater than about 5 mm may indicate abnormally high ICP.

ONSD measurements alone, however, do not provide reliable estimates of ICP, as the relationship between ONSD and ICP is not known for every individual case because of natural biovariation between individuals in normal optic nerve diameter and in tissue mechanical elasticity. Accordingly, ICP conclusions using ONSD measurements alone regarding elevated ICP are qualitative at best and are not always reliable. While ONSD measurement is easily performed, the concern for variability in patients' anatomy and physiology have limited its widespread use.

FIG. 1 illustrates various views of the eye. First is shown a sagittal histologic section of the optic nerve head and surrounding tissue (top) and a transverse histologic section of the optic nerve head (bottom). In both images, the subarachnoid space completely surrounds the optic nerve. The right hand side of FIG. 1 is an ultrasound image of a normal optic nerve sheath. ONSD may be defined as the distance between the two (white) crosshairs in the image.

A method for improving upon the ONSD-based measurement would be useful if it could remove uncertainty inherent in ONSD measurements that are close to the upper limit for ONSD, (e.g., patients that have an relatively small ONS may have an EICP that does not increase the ONS to greater than 5 mm) A method for improving upon the ONSD-based measurement would be useful if it could remove uncertainty for patients with EICP less than 30 mmHg who would nonetheless benefit from medical intervention or from additional monitoring.

Description

In a first embodiment, the claimed invention provides methods suitable for assessing a subject's ICP. The disclosed methods suitably include locating a periocular blood vessel; locating the optic nerve; obtaining optic nerve sheath diameter and blood flow information from a periocular blood vessel; and assessing intracranial pressure based on the optic nerve sheath diameter and blood flow information.

Periocular blood vessels are vessels within the cranium that are located within or close to the eye. Examples of periocular blood vessels include the ophthalmic artery, the central retinal artery and vein, the lacrimal artery, posterior ciliary arteries, superior and inferior ophthalmic veins, and middle cerebral artery. Locating a periocular blood vessel is suitably performed by imaging the vessels that supply the globe and exit the cranium through the optic canal or cavernous sinus Locating the optic nerve is suitably performed by identifying in images the anatomical structure resembling a cable that exits the cranium through the optic canal and connects the globe to the brain. Auditory signals without imaging may also be used to indicate that a vessel has been identified.

Optic nerve sheath diameter information may be collected by B-mode ultrasound, or other imaging modalities (e.g., ocular coherence tomography). Blood flow (e.g., velocity, pressure) information is suitably obtained via Doppler ultrasound or by other means known to those of skill in the art.

In some embodiments, at least one of optic nerve sheath diameter and blood velocity information is obtained with ultrasound, x-ray, magnetic resonance imaging, computed tomography, optical coherence tomography, or some combination thereof. Ultrasound—particularly Doppler ultrasound—is considered an especially suitable method for gathering this information.

Obtaining ONSD, blood velocity information, or both, is suitably accomplished noninvasively. As discussed elsewhere herein, invasive methods of measuring ICP pose a number of drawbacks to their subjects. Noninvasive ways of gathering ONSD and blood velocity information (e.g., ultrasound) are considered especially suitable for application to the claimed methods. The methods may be performed so as to save or record information on a computer-readable medium or onto other physical medium, such as a flash drive, a hard drive, a film, a printout, and the like.

A variety of blood flow (e.g., velocity) parameters are suitable. Pulsatility index ("PI"), resistivity index ("RI"), systolic velocity, diastolic velocity, and the like are all suitable velocity indicia for use in the claimed methods. The claimed methods may also use two or more of these indicia; for example, the methods may account for PI and RI measurements. PI is considered a particularly suitable velocity parameter for use in the claimed methods.

Optic Nerve Sheath Diameter ("ONSD")

The methods also suitably include comparing the measured optic nerve sheath diameter to a threshold or critical value. This threshold or critical value is selected so as to separate typical ONSD values from pathologic ONSD values associated with elevated ICP. The threshold value may be adjusted to account for anatomical ONSD variations between individuals.

An approximately normal ONSD (i.e., an ONSD value for an individual who does not suffer from EICP) is about 3.5 mm. The range for a threshold ONSD value (i.e., a value that is on the border between normal and abnormal) can be in the range of between about 5.0 to about 5.7 mm.

The choice of an optimal threshold value depends on a number of variables. One such variable is the specificity of the test for elevated ICP. A comparatively high threshold ONSD value of 5.7 mm has been reported by studies as a threshold that ensures a near 100% certainty of determining elevated ICP. Unfortunately, 5.7 mm is not as sensitive (~74%) as lower thresholds reported by studies in the 4.5 to 5 mm range.

Thus, a lower threshold figure has the potential of indicating a false positive for EICP. To overcome the reduced sensitivity of a high threshold, blood velocity parameters are—as described further herein—used to increase the sensitivity for ONSD measures between normal and threshold.

Blood Flow

The methods also suitably include comparing the gathered flow information (e.g., velocity, PI, RI) to a control value. Blood velocity in blood vessels (including those vessels associated with the optic nerve) within the cranium is affected by intracranial pressure. Blood velocity, particularly in the arteries, is not constant for a given intracranial pressure, but varies in relation to the status of the cardiac cycle. Maximum blood velocity is termed peak systolic blood velocity, and corresponds to maximum heart contraction. Minimum blood velocity during the time that the heart is filling with blood (diastole) and is termed end diastolic blood velocity.

The periocular arteries that supply tissues of the eye pass through the CSF and are sensitive to changes in CSF pressure. The systolic and diastolic blood flow velocities are subject to a complex autoregulatory process in which the periocular arteries continue to supply sufficient blood circulation to the eye even when a patient has EICP.

As one example, the central retinal artery (CRA) and central retinal vein (CRV) travel through the central region of the optic nerve, converging at the surface of the optic nerve head. The CRA is the main supply of blood to the retinal tissues, while venous outflow of the entire retina drains through the CRV.

As pressure increases surrounding the blood circulation to the eye, the resistivity and pulsatility of the blood flow in the central retinal and ophthalmic arteries are also affected.

Querfurth et al. (Acta Neurol. Scand. 2002; 105:431-440) measured central retinal arterial pulsatility in patients with varying levels of elevated intracranial pressure. These data are shown in prior art FIG. 2. The resistivity and pulsatility indices are related measures that are defined as follows:

Pulsatility Index=(peak systolic velocity−end diastolic velocity)/mean velocity

Resistivity Index=(peak systolic velocity−end diastolic velocity)/peak systolic velocity.

Figure 2:
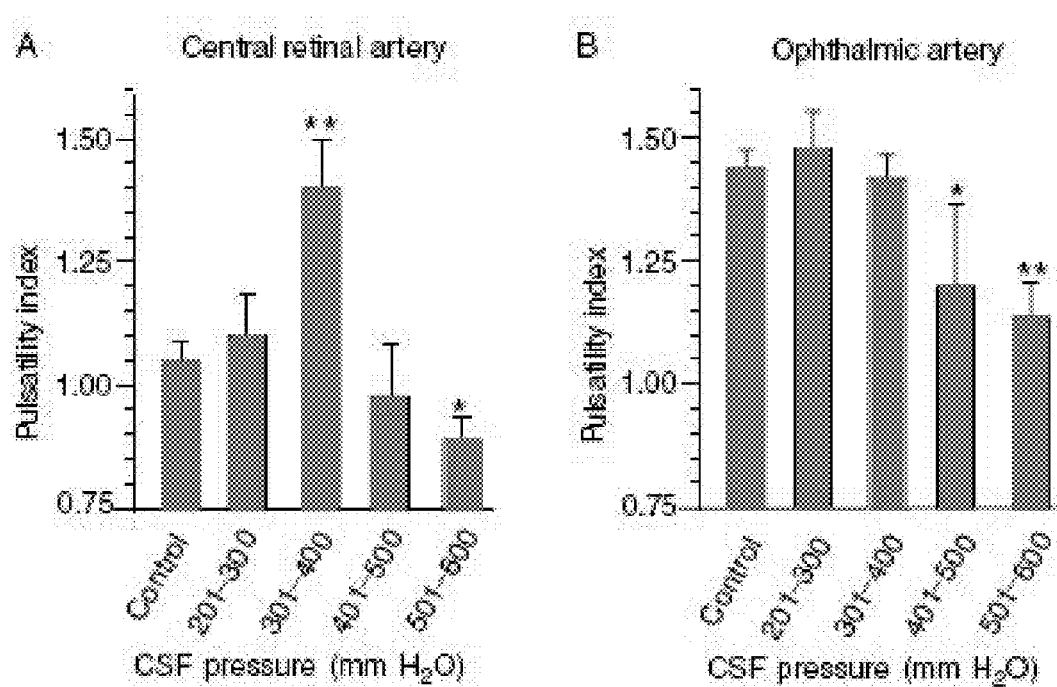
FIG. 2 illustrates Pulsatility Index ("PI") and CSF pressures in normal patients and in patients with elevated ICP.

FIG. 2 illustrates Pulsatility Index (PI) and CSF pressures in normal patients and in patients with elevated ICP. Mean pulsatility index of control subject cohort and in subgroups with 100 mm $H_2O$ increments in ICP are shown for the central retinal artery (A) and ophthalmic artery (B); n eyes=32 (control), 8 (201-300 mm $H_2O$; mild), 14 (301-400 mm $H_2O$; moderate), 4 (401-500 mm $H_2O$; severe), and 4 (501-600 mm $H_2O$; extreme).

As seen in FIG. 2, for mild to moderate ICP (15-30 mmHg), CRA pulsatility increased (panel A in FIG. 2). For moderate to severe levels of ICP>30 mmHg, the pulsatility decreased as the ICP increased. This biphasic response results in the bell-like distribution of ICP values shown in FIG. 2. Without being bound to any single theory, the phenomenon of increasing pulsatility and increasing ICP may be a result of higher inflow resistance from an increase in ambient CSF and optic nerve tension. Even at these elevated ICPs, cerebral blood flow is still maintained.

Also without being bound to any single theory, the paradoxical decrease of pulsatility at more severe ICP levels may be the result of a compensating increase in (or at least regulatory maintenance of) blood flow within the CRA. This increase in CRA flow at the moderate to severe ICP transition could result from a redistribution or diversion of blood, from an increasingly hypertensive and underperfused cerebrum, into the ophthalmic circulation. Thus, estimating ICP based on PI or RI alone is less than optimal, as a particular value of PI or RI may, as shown in FIG. 2, occur at two different ICPs.

Following a head injury, ICP above 20 mmHg is considered abnormal and possibly dangerous. Aggressive treatment is usually started at ICP values of 25 mmHg or greater.

ICP values above 10 mmHg may be considered abnormal, but not necessarily dangerous; patients with such ICP values may warrant additional monitoring. ICP pressures of from 0 to 6 mmHg are generally considered normal in the literature.

For patients with ICP of 22-30 mmHg, CRA pulsatility increased significantly compared to patients with lower pressures. Using elevated ICP as a metric, an ICP assessment device must determine if the patient has an ICP of more than about 20 mmHg, which will in turn assist the field medic in determining the best immediate course of action for the patient.

A scoring algorithm is described below which has a range of values from zero to five. Zero being minimal elevated ICP and five being a extremely elevated ICP. A score of 3 would represent a threshold at which intervention may be initiated.

Blood velocity can be characterized in a number of ways, for example pulsatility index ("PI"), resistivity index ("RI"), peak systolic velocity ("PSV"), end diastolic velocity ("EDV"), mean arterial velocity ("MAV"), or combinations of these.

Blood velocity information may be quantified using a dimensionless index such as pulsatility index, resistivity index or both. When compared to a control value, this blood velocity information assists in indicating whether elevated intracranial pressure exists.

One such dimensionless index is the pulsatility index. That index is, as explained elsewhere herein, defined as:

$$PI = \frac{PSV - EDV}{MAV}$$

The dimensionless resistivity index ("RI") is defined as:

$$RI = \frac{PSV - EDV}{PSV}$$

Both PI and RI are measures for downstream vascular resistance and may be obtained via Doppler ultrasound readings. As the resistance to flow increases downstream from where the Doppler wave is recorded, the pulsatility of the waveform increases and both PI and RI will increase.

A normal PI for the central retinal artery (CRA) is about 1.04, and for the ophthalmic artery is 1.43. A normal RI for the CRA is 0.60, and for the ophthalmic artery (OA) is 0.73 [Querfurth 2002].

Some other examples of suitable flow velocity metrics are the peak systolic and end diastolic velocities. A normal PSV for the CRA is 11.69 cm/s, and for the OA is 42.16 cm/s. Normal EDV for the CRA is 4.38 cm/s and for the OA is 11.42 cm/s. Normal MAV for the CRA is 6.79 cm/s and for the OA is 21.67 cm/s.

As intracranial pressure increases, there is a diversion of blood flow from the increasingly hypertensive and underperfused cerebrum into the ophthalmic circulation. For moderate levels of elevated intracranial pressure (e.g., approximately 22-30 mmHg), blood flow velocity parameters can be significantly different. For example, CRA PI and MAV for moderately elevated ICP are 1.39 and 4.48 cm/s, respectively. OA MAV for moderately elevated ICP is 17.47 cm/s. For extreme levels of elevated ICP (approximately 37-44 mmHg), CRA PI and MAV are 0.80 and 8.81 cm/s, respectively. OA PI for extreme levels of elevated ICP was 1.19.

Other flow velocity parameters include the mean of systolic and diastolic velocities or the difference between the systolic and diastolic velocities. Some of these parameters cross-correlate with each other. For example, central retinal end diastolic velocity and mean arterial velocity are correlated to the central retinal arterial pulsatility and central retinal venous velocity.

Figure 3:
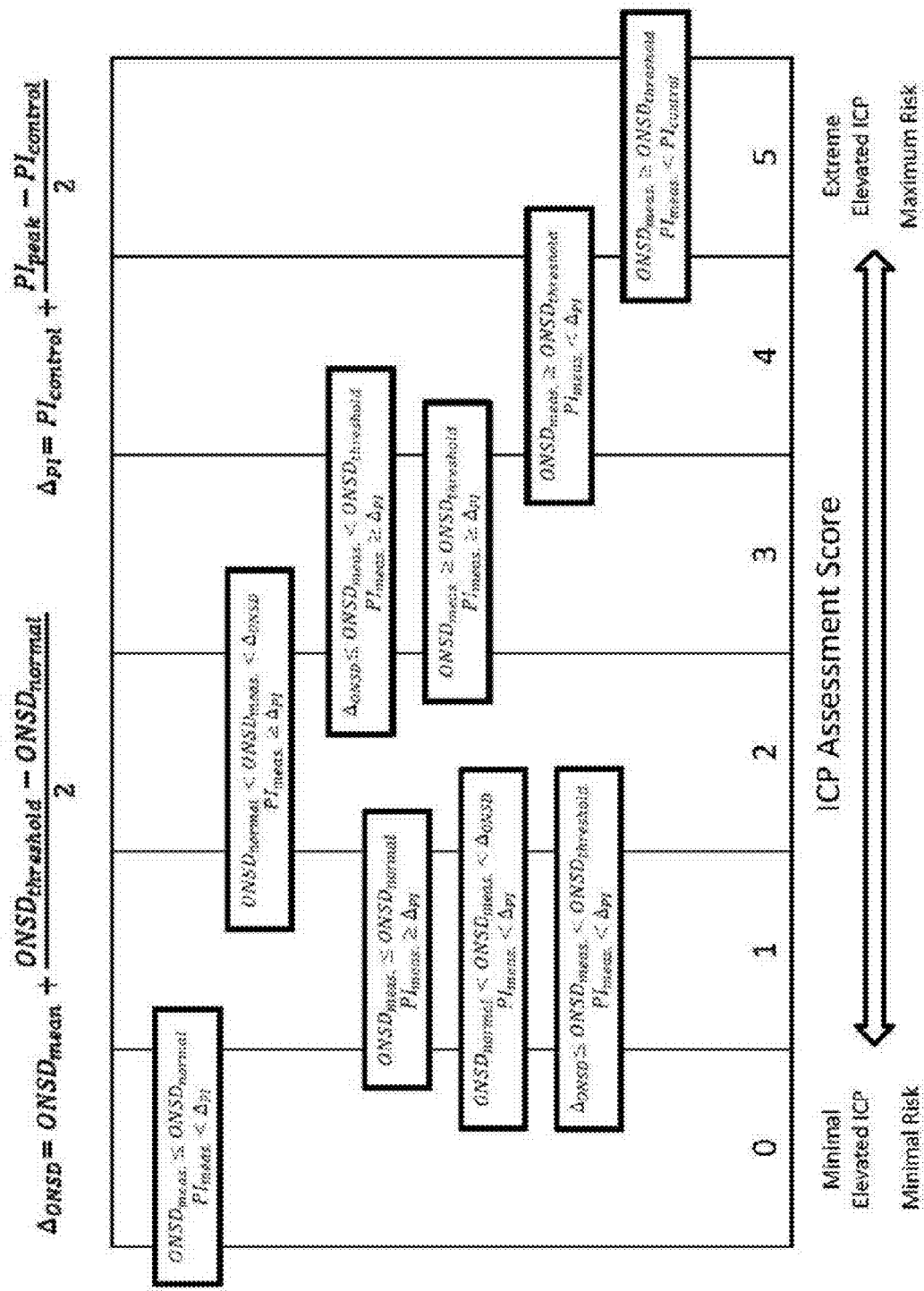
FIG. 3 illustrates an algorithm for determining an ICP assessment score based on various measurements and input values.

The methods also suitably include assigning a score value to the subject based on a combination of the optic nerve sheath diameter and blood velocity information. This combination can be a particular mathematical combination of the measured data, e.g., score=$(10 \times ONSD)+(5 \times PI)$. The score is then suitably correlated to the subject's estimated intracranial pressure, as shown in FIG. 3 and as described in additional detail elsewhere herein. The score can also be a qualitative measure, as explained below and as illustrated in FIG. 3.

FIG. 3 illustrates one application of the claimed methods, and sets forth an algorithm for determining the ICP Assessment Score based on two measurements and four input values. The score effectively correlates to the subject's estimated intracranial pressure and risk level, and is normally on a scale of zero to five, where zero corresponds to minimal risk (no or minimal elevated ICP) and five corresponds to maximum risk (extreme elevated ICP).

As shown in the figure, the input values are $PI_{control}$, $PI_{peak}$, $ONSD_{norm}$, and $ONSD_{threshold}$. These selected values are based on clinical studies and observations of patients with and without elevated ICP. $PI_{control}$ is equal to approximately 1.04, which is considered a normal PI for patients without elevated ICP. $PI_{peak}$ is equal to approximately 1.39 and corresponds to patients with moderate elevated ICP (e.g., 22 mmHg to 30 mmHg). $ONSD_{threshold}$ ranges from 5.0 mmHg to 5.7 mmHg and corresponds to severely elevated ICP of 30 mmHg or greater. $ONSD_{norm}$ corresponds to normal ONSD in patients (3.5 mm).

These input values can be based on clinical data and may be updated to reflect additional clinical data. As described elsewhere herein, ICP cannot be fully assessed using only ONSD, as anatomic variability makes it impossible to distinguish between distended optic nerve sheaths due to minimal or moderate levels of ICP elevation and undistended but larger than normal optic nerve sheaths.

The two measured values used in the illustrated algorithm—$PI_{meas}$ and $ONSD_{meas}$—can be obtained in a variety of ways. Devices that collect data using B-mode (ultrasonography) and Doppler ultrasound are suitable for collecting these measured values.

ONSD is suitably measured approximately 3 mm posterior of the globe, and can be measured using a 7-10 MHz ultrasound probe in a B-mode. Devices designed for the ophthalmology (e.g., devices made by Alcon, Sonomed, and Tomey) are all considered suitable. Hospital bedside ultrasound imaging devices such as the GE Logiq series and Phillips Agilent Image Point series can be used to measure ONSD as well. To measure PI, the central retinal artery was chosen because of its comparative sensitivity to moderate elevated ICP. $\Delta ONSD$ is defined, in this example, as the midpoint between $ONSD_{norm}$ and $ONSD_{threshold}$.

The quantity $\Delta PI$ is defined as the midpoint between $PI_{control}$ and $PI_{peak}$. The methods thus, in one embodiment, involve assessing two or more values (at least ONSD and one blood velocity parameter) to calculate a score that correlates to a subject's level of ICP.

While FIG. 3 uses PI as the blood velocity component of the algorithm, the claimed invention is not limited to PI, and other blood flow or velocity values (singly or in combination with one another) may be used. The blood flow value may be an actual measured velocity, or may be a dimensionless group (e.g., PI), or even a value that has non-velocity units (e.g., a force).

In a screening or triage situation based on the algorithm of FIG. 3, scores of 0 and 1 represent minimal risk to a patient. Patients exhibiting such scores would have little to no risk of elevation in ICP and would not require medical intervention.

Referring to the lowermost box given a score of 1, such patients may have abnormally large ONS relative to the population; although their ONSD is almost to the threshold, the PI indicates an ICP that is less than moderate EICP. Scores of 2 and 3 represent a moderate risk of elevated ICP, and reflect ICP that may warrant close monitoring and possible pharmaceutical or other non-surgical intervention.

Examples of pharmaceutical interventions include osmotic agents such as mannitol and hypertonic saline that are administered intravenously to reduce ICP. Examples of other non-surgical, non-pharmacological interventions include hyperventilation, hyperbaric oxygen therapy, hypothermia, and sedation and analgesia to decrease metabolic demands of the brain.

Referring to the bottommost box given a score of 3, patients classified in this box may have an abnormally large ONS relative to the population; although their ONSD is greater than the threshold value, the PI indicates a moderate level of EICP instead of severe.

Patients with scores of 4 and 5 may require immediate medical intervention and may require surgical intervention to relieve a severe level of ICP. Referring to boxes that are assigned scores of 4 or 5, patients in these categories may receive medical intervention in the form of CSF drainage through a cranial shunt, lumbar drain, or decompressive craniectomy.

In addition to the utility of a stand-alone score for screening purposes, serial measurements can identify trends in the ICP assessment score that can be used for monitoring purposes to track a patient's condition and affect treatment choices, including selection of a triage plan based on the assessment of intracranial pressure.

For example, a physician can monitor a subject's ICP over time by observing whether the subject's assessment score increases or decreases over time. The physician can also apply the claimed methods to determine whether and how a patient's ICP score responds to treatment. The ICP score may also be used as a diagnostic tool that allows physicians to determine, by observing the changes in the ICP score, the effectiveness of various treatments. A physician can also determine, by monitoring an ICP score, whether a particular treatment for an unrelated condition has any effect on the patient's ICP.

Without being bound to any specific theory or ranges, scores of 0 and 1 in the embodiment shown in FIG. 3 are associated with ICP pressures of less than 15 mmHg Scores of 2 and 3 are associated with ICP values of between 15 mmHg and 30 mmHg Scores of 4 and 5 are associated with ICP pressures greater than about 30 mmHg A score of 5 suggests a risk of high ICP; a score of 1 is considered to have low ICP risk.

The claimed invention also provides devices. These inventive devices suitably include a component (e.g., a probe, such as a hand-held wand type probe) configured to obtain optic nerve sheath diameter, blood velocity information, or both from a periocular blood vessel and a component configured to, based on the optic nerve sheath diameter and blood velocity information, produce an assessment of the subject's intracranial pressure.

The device may include two separate components (e.g., a separate probe for performing each of these tasks) or may include two components disposed inside a single probe, so that the user can use a single probe device to gather necessary information. In some embodiments, the device may include only a single component that acts to gather both pieces of information such that the device includes only a single component. Such a device might be one where a single ultrasound probe gathers ONSD and blood flow velocity.

A suitable component may be an ultrasound transducer, an x-ray emitter, a magnetic resonance imager, a computed tomography scanner, optical coherence tomography scanner, and the like. Ultrasound transducers are considered especially suitable. The device may be a handheld instrument that includes a probe (e.g., an ultrasound probe) that is capable of obtaining optic nerve sheath diameter information. This may be obtained by collecting an ultrasound image of the eye under analysis, which image can then be interpreted by a user to arrive at an ONSD estimate. Existing ultrasound devices, such as those made by General Electric (www.ge.com) and by Multigon (www.multigon.com) are considered suitable.

In some embodiments, the component is configured so as to gather image information from the subject eye and calculate ONSD size based on the image in an automated fashion. A component (or the device as a whole) may also be configured to obtain blood flow (e.g., PI) information from a subject in an automated fashion, with little to no user involvement.

A component may be connected to a computer or other display so that the user may visualize the data being gathered by the component. The device may be configured to provide audio or visual instructions to the user to allow more precise positioning and operation of the device.

The device may also include a display screen, a printer, or other component to allow the user to visualize and analyze information collected by the device. The device may include a hard drive or other memory unity to allow recordation of data. The device may be connected to an information network, such as a hospital records system, so as to allow remote viewing and analysis/interpretation of information gathered by the device.

The device may also include a transmitter or radio system to as to allow the device to transmit information to a receiver. This enables a remote user—such as a physician located at a hospital—to view and interpret information that has been gathered in the field. The information-gathering probe may be wired or wirelessly connected to a computer or other device for data analysis. Alternatively, the probe may include an on-board analysis device or display device so as to allow the user to visualize or receive data on-site.

The components may be computer chips or hardware that reside on a single probe or other sensing device. Alternatively, the components may each be their own separate probe, where one probe is configured to collect ONSD information, and the other probe is configured to collect blood velocity information. In such an embodiment, the device may include a central unit having two probes connected thereto.

The device may also include a central unit having a probe connected thereto. The devices used in the claimed methods can be configured to output a visual and/or audio warning for an operator to determine the proper medical intervention for a patient that is being screened for EICP. In some embodiments, the probe itself may include a display device (e.g., a video screen or readout) so as to render the device portable.

Components that gather data by way of ultrasound are considered especially suitable. Physicians are familiar with ultrasound technology and it is one of the most widely used diagnostic tools in modern medicine. Compared to magnetic resonance imaging ("MRI") and computed tomography ("CT"), ultrasound technology is also relatively inexpensive and portable, although MRI and CT devices can take measurements of the ONS and have a higher resolution image than ultrasound, but are not portable.

Measurements on the eye are also ideally suited for ultrasound because the globe of the eye is fluid filled, which presents a suitable interface and medium for ultrasound to visualize the optic nerve. ONSD measurements can be obtained using B-mode ultrasound imaging and blood velocity information can be obtained using Doppler ultrasound.

To perform these ultrasound measurements, an ultrasound probe of a suitable frequency is used. Lower frequency probes allow for deeper tissue penetration, while higher frequency probes allow for more imaging resolution.

ONSD measurements are taken 3 mm behind the eye, requiring a total tissue penetration of approximately 25 mm. This is the depth required for Doppler ultrasound measurements of the central retinal artery as well. Ophthalmic artery insonation requires penetration of approximately 40 to 50 mm. For this amount of tissue penetration, an ultrasound probe of between 7 MHz and 10 MHz is preferred. The devices may feature imaging and Doppler capabilities built in, such that the operator can use the same probe and machine. Other devices may have only B-mode imaging (2D), the minimum required to make a ONSD measurement, with still other units having only Doppler ultrasound, which can only measure the velocity data. Ultrasound devices may operate at one or more frequencies. The deice may also include a rechargeable battery, a removable memory device (e.g., a flash memory card), and the like.

These measurements can be performed by multifunctional bedside ultrasound units that are commonly found in trauma centers. One such unit is the GE Healthcare Logiq P5. By taking these measurements and using this method, a rapid assessment of ICP can be performed to aid the physician in determining if medical intervention is appropriate for a patient with a suspected head injury.

For a multifunctional unit, the operator takes an image of the desired target area, in this case the ONS, and then uses a distance measurement tool. Such a tool can be placing two crosshairs on an image and measuring the distance between the crosshairs.

The operator identifies the ONS and then manually marks the points and then use the software to make the measurement. This is similar process to measuring anatomical features on a fetus or the size and location of a tumor.

A device may be configured so as to automate the measurement by a combination of hardware mounts to ensure proper probe alignment and software algorithms to process the images to get the desired measurements. The process for obtaining Doppler velocity data is similar to the distance measurement. A 2D image of the target area is made by the operator. The vessel of interest is located and selected by the operator in the software and the ultrasound system outputs the velocity data, such as PI, RI, PSV, EDV. The device may generate a time history of the blood velocity in the selected area.

The device may also be configured to collect ONSD and blood velocity information that outputs an ICP assessment score based on an algorithm, such as that set forth in FIG. 3. Existing ultrasound systems have not been designed to locate the appropriate anatomy, take the needed measurements, and calculate an ICP assessment score. The device may be configured to collected ONSD information in an automated fashion, e.g., by autofocus or by automated mage analysis techniques that locate the optic nerve and use edge detection or pattern recognition.

Such devices accomplish this collection by a combination of alignment tools and software algorithms to identify the proper target areas to collect data. The probe device may include a headband or other means for securing the probe to the head or face of the subject, so as to maintain the device in proper orientation for data gathering. A single probe may include separate components, one to measure ONSD information and one to gather blood velocity information. The components may gather information sequentially or simultaneously. As described elsewhere herein, the device may include a single component that gathers ONSD and blood flow information.

The components for obtaining ONSD and blood information could be a combination of an ultrasound transducer, and x-ray emitter, a magnetic resonance imaging (MRI) scanner, or a computed tomography (CT). The preferred component would be an ultrasound transducer configured such that both B-mode imaging and Doppler modalities are combined into one probe for a dedicated ICP assessment device. Such probes can interface with handheld computers, so the operator can scan a patient in the field using battery power and minimal physical footprint. ICP assessment can occur immediately after trauma, before patient transport and evacuation has to be arranged. Existing ultrasound platforms can be modified into an ICP assessment device that incorporates ONSD and blood velocity measurements.

These modifications can be done electronically in phased array ultrasound probes to collect both two-dimensional (B-mode) and continuous wave Doppler information. One illustrative electronic modification uses a time sharing arrangement in which the transducer rapidly switches back and forth from one type of examination to the other.

A physical modification may be done by mounting two ultrasound modalities together, for example a B-mode linear array of ultrasound transducers and a Doppler pulse wave piezoelectric crystal aligned so that the combined probe can target the same area of interest.

Also disclosed are systems for assessing a patient's ICP. These systems suitably include a first device configured to obtain, from a subject, optic nerve sheath diameter information; a second device configured to obtain, from a subject, blood velocity information from a periocular blood vessel, and the system being further configured to, based on the optic nerve sheath diameter and blood velocity information, produce an assessment of the subject's intracranial pressure.

As described elsewhere herein, ONSD and velocity information may be collected by ultrasound transducers, x-ray emitters, magnetic resonance imagers, computed tomography scanners, optical coherence tomography scanners, and the like. The system may include one or more of these devices to gather information from the subject. Ultrasound transducers are considered especially suitable devices.

The system may include two probes (one probe to perform ONSD measurement and one probe to perform blood velocity measurement). The two devices may be in independent housings; alternatively, the two devices may be contained within a single housing. For example, the system may include a housing inside which are disposed two different ultrasound transducers, one of which is configured to collect ONSD information, and the other being configured to collect blood velocity information. The housing might also contain an ultrasound transducer and a CT device. The probes may be used sequentially (gathering one piece of information at a time) or simultaneously (gathering ONSD and blood flow information at the same time).

The system is suitably adapted to assess the patient's ICP based on ONSD or blood velocity information. This adaptation may be effected by including an automation routine in the system that assigns a score to the subject based on the measured ONSD and a blood velocity metric, such as PI or RI. The score may be assigned on the basis of a mathematical operation on the ONSD and velocity information, or may be assigned based on the application of an algorithm to the information, such as the algorithm shown in FIG. 3.

As one non-limiting example, the system can determine to which "box"/score (shown in FIG. 3) a given patient belongs. The system can then output that score to the user. This output can be accompanied by (or even be in the form of) a visual or audio alert, which alert may differ depending on the patient's ICP assessment score. The system may also provide the user with audio or visual cues or instructions regarding the system's use and operation.

The system may include a central processing unit that is connected to one or more probes. The central processing unit is suitably configured to assess the patient's ICP based on the data collected by the devices.

The system may be present in a kit form. The system may include gels or other media for facilitating probe engagement with the subject (e.g., a gel to facilitate transmission of ultrasound to the subject). The kit suitably includes instructions for use, as well as instructions for interpreting the output of the system. The kits may include carrying cases and the like to store and transport the system.

What is claimed:

1. A method, comprising:
   providing an imaging device operatively connected to an intracranial pressure estimation component that comprises a processor;
   operating the imaging device so as to obtain optic nerve sheath diameter information and blood velocity information from a periocular blood vessel of a subject;
   outputting the optic nerve sheath diameter information and blood velocity information to the intracranial pressure estimation component; and
   executing instructions on the processor of the intracranial pressure estimation component,
   the instructions including receiving the optic nerve sheath diameter information and blood velocity information, estimating an intracranial pressure of the subject based on a mathematical combination of the optic nerve sheath diameter information and blood velocity information, and outputting the estimate of the intracranial pressure of the subject.

2. The method of claim 1, wherein the blood velocity information comprises pulsatility index, resistivity index, systolic velocity, diastolic velocity, or any combination thereof.

3. The method of claim 2, wherein the blood velocity information comprises pulsatility index, resistivity index, or both.

4. The method of claim 1, wherein the mathematical combination comprises multiplying at least one of the optic nerve sheath diameter or the blood velocity information by a factor, adding together the optic nerve sheath diameter or the blood velocity information, comparing at least one of the optic nerve sheath diameter or the blood velocity information to a control value, or any combination thereof.

5. The method of claim 1, wherein the estimating further comprises comparing the blood velocity information to a control value.

6. The method of claim 4, further comprising assigning a score value to the subject based on the mathematical combination of the optic nerve sheath diameter and blood velocity information.

7. The method of claim 6, wherein the score value correlates to the subject's estimated intracranial pressure.

8. The method of claim 1, wherein at least one of optic nerve sheath diameter and blood velocity information are obtained with ultrasound.

9. The method of claim 8, wherein the blood velocity information is obtained with Doppler ultrasound.

10. The method of claim 8, wherein the optic nerve sheath diameter is obtained with ultrasound.

11. The method of claim 1, further comprising selection of a triage plan based on the estimate of intracranial pressure.

12. The method of claim 1, wherein the obtaining optic nerve sheath diameter and blood velocity information from a periocular blood vessel is performed noninvasively.

13. The method of claim 1, further comprising placing the estimate of intracranial pressure on a computer-readable medium.

14. The method of claim 1, wherein the optic nerve sheath diameter and blood velocity information from a periocular blood vessel of a subject are collected in an automated fashion.

15. The method of claim 1, wherein at least one of the optic nerve sheath diameter information and the blood velocity information are obtained with ultrasound, x-ray, magnetic resonance imaging, computed tomography, optical coherence tomography, or any combination thereof.

* * * * *